United States Patent [19]

Bluhm et al.

[11] 4,227,532
[45] Oct. 14, 1980

[54] DEVICE FOR CRUSHING CALCULI IN THE URINARY BLADDER

[75] Inventors: Karl H. Bluhm; Helfrid Kunath, both of Hamburg, Fed. Rep. of Germany

[73] Assignee: U.S. Philips Corporation, New York, N.Y.

[21] Appl. No.: 893,069

[22] Filed: Apr. 3, 1978

[30] Foreign Application Priority Data

May 28, 1977 [DE] Fed. Rep. of Germany ....... 2724324

[51] Int. Cl.³ .............................................. A61B 17/22
[52] U.S. Cl. ................................................... 128/328
[58] Field of Search ................ 128/328, 329 R, 24 A, 128/7

[56] References Cited

U.S. PATENT DOCUMENTS

| 2,227,727 | 1/1941 | Leggiadro | 128/328 |
| 3,557,793 | 1/1971 | Ediny et al. | 128/328 |
| 3,785,382 | 1/1974 | Schmidt-Kloiber et al. | 128/328 |
| 3,792,701 | 2/1974 | Kloz et al. | 128/328 X |

FOREIGN PATENT DOCUMENTS

| 2020345 | 3/1975 | Fed. Rep. of Germany | 128/328 |
| 2349120 | 4/1975 | Fed. Rep. of Germany | 128/328 |

Primary Examiner—Robert W. Michell
Assistant Examiner—Michael H. Thaler
Attorney, Agent, or Firm—Marc D. Schechter

[57] ABSTRACT

A device for crushing calculi in the urinary bladder, comprising a bundle of elongate, flexible lithotriptors which are accommodated in a ureter catheter and on whereto reciprocating movements can be imparted by a drive system.

1 Claim, 8 Drawing Figures

DEVICE FOR CRUSHING CALCULI IN THE URINARY BLADDER

BACKGROUND OF THE INVENTION

The invention relates to a device for crushing calculi in the urinary bladder, comprising an elongate, flexible lithotriptor which extends in a ureter catheter which can be introduced into the body of a patient, it being possible to impart longitudinal reciprocating movements to said lithotriptor by means of a drive system which remains outside the body.

A device of this kind is known from U.S. Pat. No. 3,785,382 (German Auslegeschrift No. 22 23 319). By means of the longitudinally vibrating lithotriptor it is possible to crush calculi in the urinary bladder, but a problem remains in that the duration of crushing is comparatively long and this is a substantial burden for the patient.

SUMMARY OF THE INVENTION

An object of the invention is to provide a device for crushing calculi in the urinary bladder into several relatively large fragments which, enables faster crushing, particularly of large calculi, and in addition to crushing, allows pulverizing of the calculus material into small powder like particles.

To this end, the device in accordance with the invention is characterized in that the ureter catheter surrounds a bundle of reciprocatable lithotriptors which can be activated independently of each other. As a result of the independent activation of a number of lithotriptors, cutting, drilling, or crushing effects can be realized. Consequently, operation according to the requirements of the moment is always possible, so that the time required for lithotrity can be reduced. A bundle comprising, for example, seven lithotriptors in a circular arrangement has a diameter which does not exceed the diameter of a catheter.

In a further embodiment of the invention, each lithotriptor can be reciprocated by its own electromagnetic drive. When the drives are arranged in a row one behind the other, a comparatively small, handy and light device is realized. The electromagnetic drive offers the advantage that low voltages and currents can be used in the vicinity of the patient and that activation can be simply controlled. The control of the movement frequency between 1 Hz and 300 Hz offers further operation variations adapted to the given circumstances. The frequency may be of importance, for example, for crushing calculi consisting of different component materials.

In a further embodiment of the device according to the invention, the ureter catheter can be replaced by a ureter catheter accommodating a different geometrical arrangement of the bundle of individual lithotriptors. For example, a ring of lithotriptors may be arranged around a central lithotriptor. Such a device is preferably used for drilling and pulverizing. In a further geometrical arrangement, the individual lithotriptors are arranged in a row. The fracturing of larger calculi can be substantially improved by means of this arrangement.

In a further embodiment of the device according to the invention, the active ends of the lithotriptors are conically pointed. As a result of the conically pointed shape, the crushing effect is enhanced, because higher forces can act on the calculus. The length of the conical tip of the lithotriptors equals the part of the lithotriptors which can be slid out of the catheter. A further advantage of the conical tip is that jamming of the lithotriptors in the calculus during crushing is prevented. A further variant of the invention allows adjustment of the stroke of the lithotriptors. The effect on the calculus can thus also be changed.

In the stationary condition the ends of the lithotriptors are slightly withdrawn into the catheter in order to avoid damaging of the bladder wall. The ends of the lithotriptors are made to protrude from the catheter, into an operating position, when pressure is exerted on a button. This means that the catheter can be made to contact the calculus, after which crushing can be started by means of pressure exerted on the button. The escape of smaller calculi is thus also prevented in many cases.

Finally, it is advantageous that the ureter catheter be used in combination with a calculus holder and an optical device. The attending physician can then oversee the working area and fix the remainders of the calculus or the calculi so that they do not escape the influence of the lithotriptors.

Embodiments of the device in accordance with the invention will be described in detail hereinafter with reference to the accompanying diagrammatic drawing.

DESCRIPTION OF THE PREFERRED EMBODIMENTS

Figure 1:
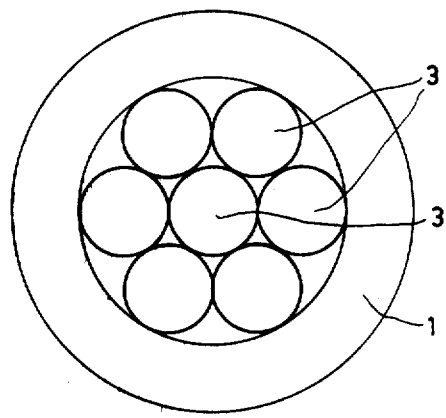
FIGS. 1 and 2 show two different geometrical arrangements of the lithotriptors in their ureter catheter.
Figure 2:
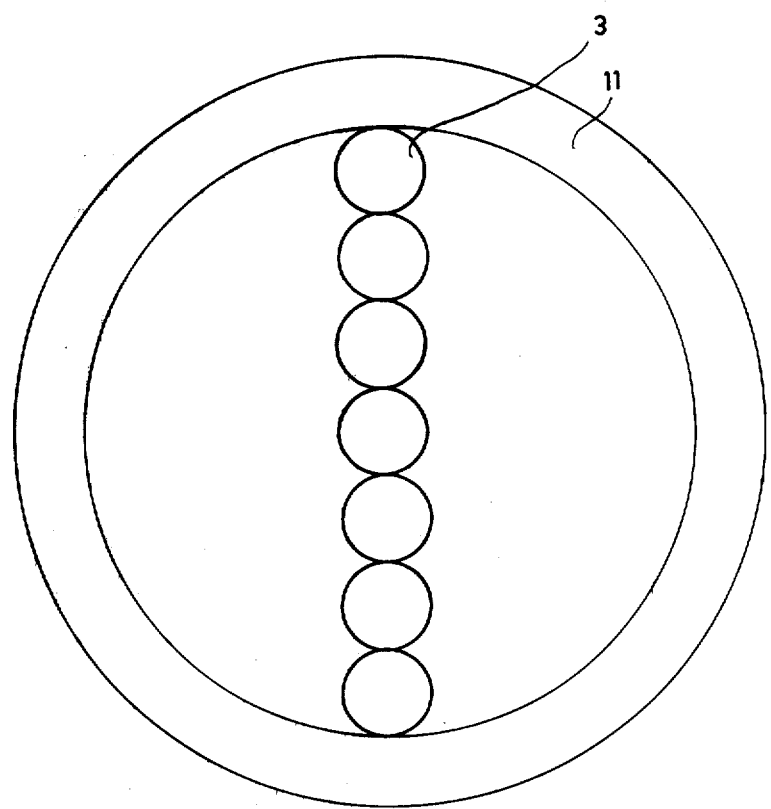

In the embodiment shown in FIG. 1, seven lithotriptors 3 are arranged in a ureter catheter 1. A ring of six lithotriptors is provided around a central lithotriptor. These lithotriptors can be made to reciprocate, independently of each other, by electromagnetic drives shown in FIG. 3. The geometrical arrangement shown in FIG. 1 is used mainly for drilling and pulverizing. FIG. 2 shows a further ureter catheter 11 in which the lithotriptors 3 are arranged in a row. This arrangement is preferably used for fracturing operations.

Figures 3, 4:
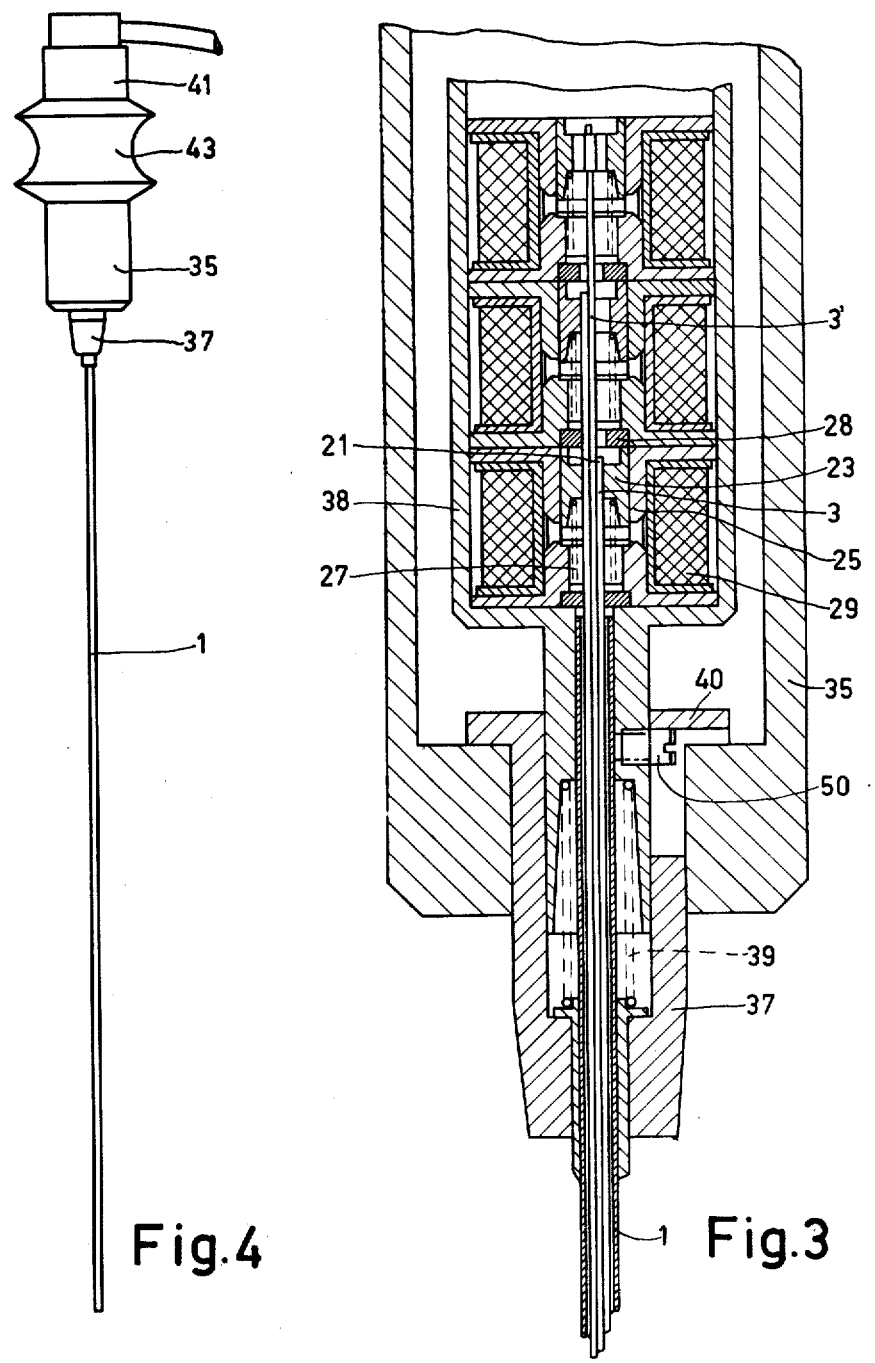
FIG. 3 shows a part of the electromagnetic drive of the lithotriptors.
FIG. 4 is an overall view of the device in accordance with the invention.
Figure 3A:
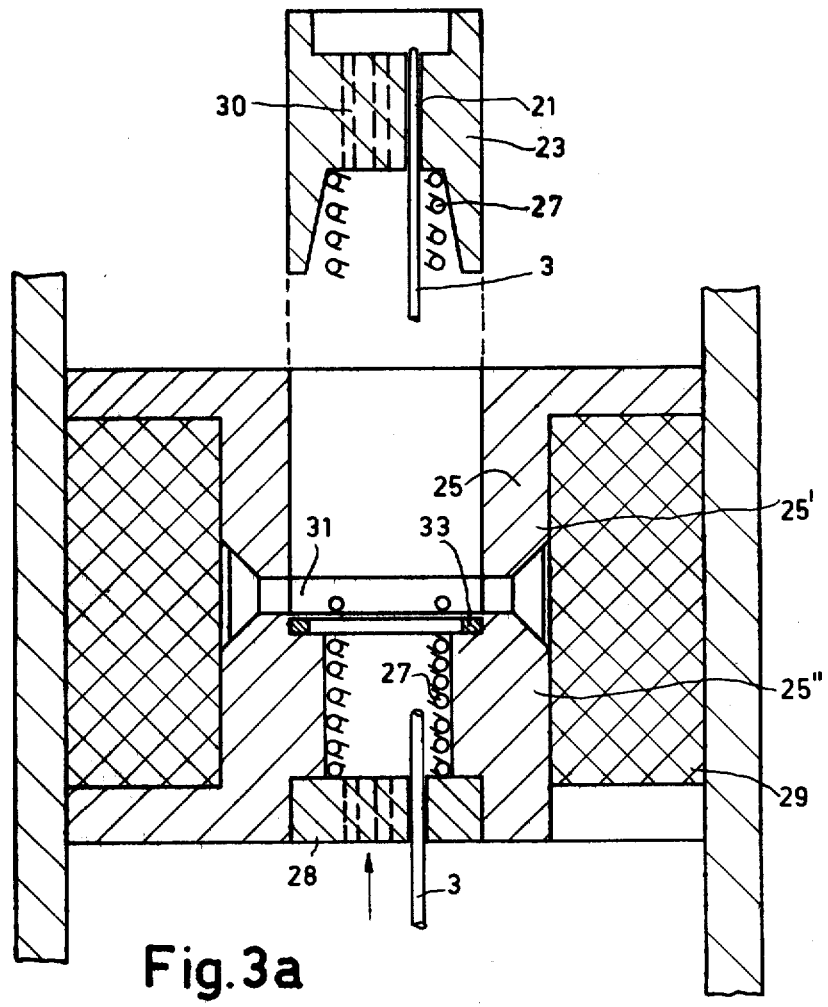
FIG. 3a is a cutaway view at an increased scale of a magnet system.
Figure 3B:
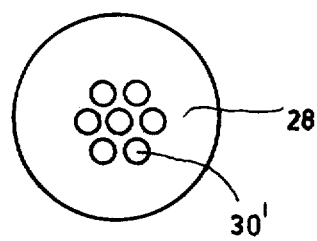
FIG. 3b is a plan view of a damping plate of the magnet drive.

FIG. 3 shows the drives for the individual lithotriptors axially arranged, one behind the other. The rear portion of the lithotriptor 3 is provided with an iron armature 23 which co-operates with a pair of magnet poles 25. A compression spring 27 ensures that the lithotriptor, or the armature 23 thereof, is withdrawn and pressed against a damping abutment 28. FIG. 3a is a cutaway view of one of the total number of seven magnetic drives which are arranged one above the other. The magnet pole of the magnetic drive consists of two pole pairs 25' and 25" which are soldered to each other and which accommodate an activation winding 29. The iron armature 23 comprises seven bores 30, six bores being concentrically arranged around the seventh bore. The end 21 of the lithotriptor 3 is soldered down in one of the bores 30. The six bores which remain open serve for guiding the six further lithotriptors which are soldered thereabove to other iron armatures. The damping abutment 28, shown in a plan view in FIG. 3b, is also provided with seven bores 30' whose diameter and mutual arrangement correspond to the diameter and the arrangement of the bores in the iron armature 23.

When the winding 29 is activated, the armature 23 is pulled through the air gap 31 between the magnet poles 25. A damping end abutment ring 33 limits the length of the stroke of the iron armature 23, thus limiting the length of the stroke of the lithotriptor 3 which is soldered to the iron armature 23. In the housing 35 of the present embodiment, seven electromagnetic drives are arranged axially one behind the other, the armature 23 of each individual electromagnetic drive supporting a lithotriptor. The electromagnets are activated, independently of each other, by way of an electronic circuit (not shown), it being possible to preselect the instant of activation and the frequency of activation in accordance with the presettings of the control apparatus or the instructions of the attending physician.

Figure 5:
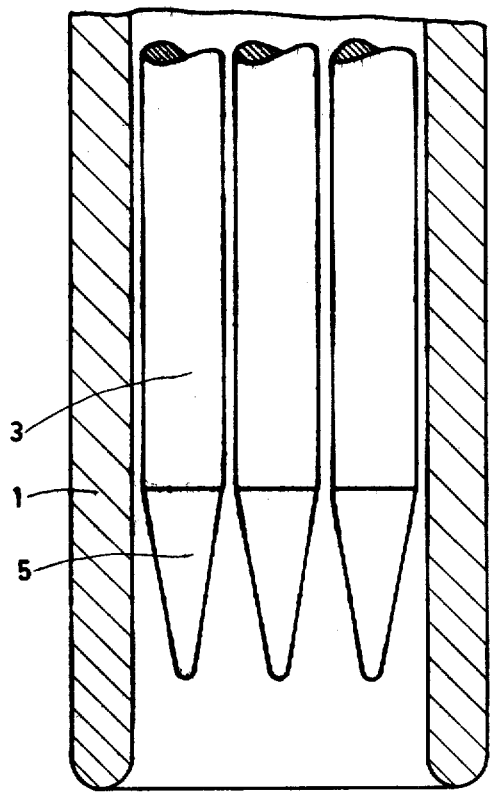
FIG. 5 shows the lithotriptors withdrawn into the ureter catheter (rest position)

FIG. 4 is an overall view of the device according to the invention. The lithotriptors 3, guided in the ureter catheter 1, can be withdrawn therein. This is possible because the ureter catheter 1 is accommodated in a holder 37 which is mounted on the housing 35. A spring 39 presses a sleeve 38, enclosing the magnetic drives with the lithotriptors 3, into the housing 35 until an adjusting screw 50 abuts against an abutment 40 (see also FIG. 3 and FIG. 6). By exerting a suitably directed pressure on a button 41, the magnetic drives with the lithotriptors 3 are slid down in the housing 35. The conical active ends 5 (FIG. 5) of the lithotriptors 3 then emerge from the end of the catheter 1. When the pressure on the button 41 is reduced, the magnetic drives and the lithotriptors 3 are automatically returned by the spring 39.

Figure 6:
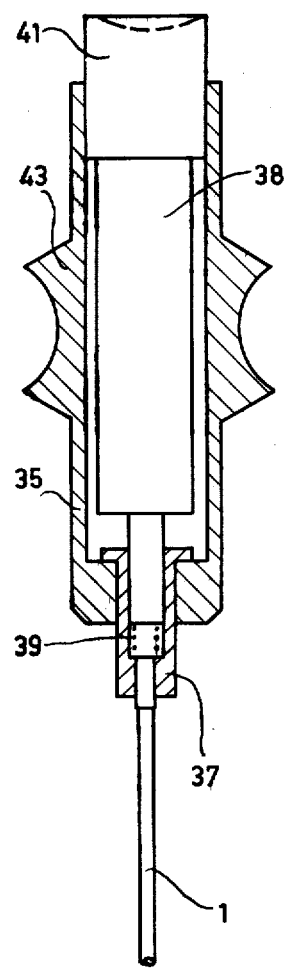
FIG. 6 is a diagrammatic sectional view of an adjusting device for the lithotriptors.

In order to facilitate operation of the device, the housing 35 is provided with a recess 43 for the fingers (FIG. 6).

What is claimed is:

1. A device for crushing calculi in the urinary bladder, comprising a bundle of independently reciprocatable, elongate, flexible lithotriptors disposed in a ureter catheter in a configuration comprising a ring of lithotriptors arranged around a central lithotriptor.

* * * * *